(12) United States Patent
Lueck et al.

(10) Patent No.: US 8,418,523 B2
(45) Date of Patent: Apr. 16, 2013

(54) CALIBRATION AND ACCURACY CHECK SYSTEM FOR A BREATH TESTER

(76) Inventors: Keith Lueck, Fenton, MO (US); Karl Wolf, Jr., Eureka, MO (US)

( * ) Notice: Subject to any disclaimer, the term of this patent is extended or adjusted under 35 U.S.C. 154(b) by 249 days.

(21) Appl. No.: 12/397,206

(22) Filed: Mar. 3, 2009

(65) Prior Publication Data

US 2010/0223975 A1   Sep. 9, 2010

Related U.S. Application Data

(60) Provisional application No. 61/033,218, filed on Mar. 3, 2008, provisional application No. 61/050,823, filed on May 6, 2008.

(51) Int. Cl.
*G01N 33/497* (2006.01)
(52) U.S. Cl.
USPC .............................................. 73/1.06; 73/23.3
(58) Field of Classification Search .................. 73/1.06, 73/23.3
See application file for complete search history.

(56) References Cited

U.S. PATENT DOCUMENTS

| | | |
|---|---|---|
| 3,889,591 A | 6/1975 | Noguchi |
| 3,948,604 A | 4/1976 | Hoppesch |
| 4,278,636 A | 7/1981 | Voigt et al. |
| 4,812,856 A | 3/1989 | Wallace |
| 4,828,886 A | 5/1989 | Hieber |
| 4,853,317 A | 8/1989 | Hayes |
| 4,877,745 A | 10/1989 | Hayes et al. |
| 5,053,100 A | 10/1991 | Hayes et al. |
| 5,092,864 A | 3/1992 | Hayes et al. |
| 5,193,738 A | 3/1993 | Hayes |
| 5,208,980 A | 5/1993 | Hayes |
| 5,227,813 A | 7/1993 | Pies et al. |
| 5,229,016 A | 7/1993 | Hayes et al. |
| 5,235,352 A | 8/1993 | Pies et al. |
| 5,334,415 A | 8/1994 | Hayes et al. |
| 5,345,256 A | 9/1994 | Stortz |
| 5,365,645 A | 11/1994 | Walker et al. |
| 5,373,314 A | 12/1994 | Everett et al. |
| 5,377,902 A | 1/1995 | Hayes |
| 5,400,064 A | 3/1995 | Pies et al. |
| 5,400,637 A | 3/1995 | Forrester |
| 5,402,162 A | 3/1995 | Fusting et al. |
| 5,406,319 A | 4/1995 | Hayes et al. |
| 5,411,602 A | 5/1995 | Hayes |
| 5,414,916 A | 5/1995 | Hayes |

(Continued)

OTHER PUBLICATIONS

Rayleigh, F.R.S., "On the instability of jets," Proceedings of the London Mathematical Society, 1878, pp. 4-13, vol. 10.

(Continued)

*Primary Examiner* — Hezron E Williams
*Assistant Examiner* — Gregory J Redmann
(74) *Attorney, Agent, or Firm* — Lewis, Rice & Fingersh, L.C.

(57) ABSTRACT

Calibration and accuracy check systems for a chemical sniffer, such as a breath alcohol tester, which utilize the dispensing of droplets with determinable concentration of alcohol and/or other liquids in a determinable number either directly to a reaction chamber, or into a carrier gas which can be sampled. The systems generally provide for accurate sample concentration being provided to the breath tester while also providing for a simplified system which can be easier to move, and require less operational complexity, than prior wet or dry calibrating systems.

17 Claims, 7 Drawing Sheets

U.S. PATENT DOCUMENTS

| | | | |
|---|---|---|---|
| 5,415,679 A | 5/1995 | Wallace | |
| 5,422,485 A | 6/1995 | Bowlds | |
| 5,424,916 A | 6/1995 | Martin | |
| 5,426,455 A | 6/1995 | Williamson et al. | |
| 5,430,470 A | 7/1995 | Stortz | |
| 5,433,809 A | 7/1995 | Pies et al. | |
| 5,435,060 A | 7/1995 | Hayes et al. | |
| 5,436,648 A | 7/1995 | Stortz et al. | |
| 5,438,739 A | 8/1995 | Granzow | |
| 5,440,332 A | 8/1995 | Good | |
| 5,444,467 A | 8/1995 | Stortz | |
| 5,461,403 A | 10/1995 | Wallace et al. | |
| 5,462,600 A | 10/1995 | Pies | |
| 5,479,684 A | 1/1996 | Murphy | |
| 5,481,285 A | 1/1996 | Pies et al. | |
| 5,498,444 A | 3/1996 | Hayes | |
| 5,505,364 A | 4/1996 | Plesinger | |
| 5,506,034 A | 4/1996 | Pies et al. | |
| 5,521,618 A | 5/1996 | Stortz et al. | |
| 5,535,494 A | 7/1996 | Plesinger et al. | |
| 5,543,009 A | 8/1996 | Hayes | |
| 5,554,247 A | 9/1996 | Pies et al. | |
| 5,557,304 A | 9/1996 | Stortz | |
| 5,557,309 A | 9/1996 | Hayes | |
| 5,563,641 A | 10/1996 | Plesinger | |
| 5,581,286 A | 12/1996 | Hayes et al. | |
| 5,604,521 A | 2/1997 | Merkel et al. | |
| 5,621,442 A | 4/1997 | Hayes et al. | |
| 5,622,897 A | 4/1997 | Hayes | |
| 5,643,353 A | 7/1997 | Wallace et al. | |
| 5,658,802 A | 8/1997 | Hayes et al. | |
| 5,666,145 A | 9/1997 | Hayes et al. | |
| 5,677,719 A | 10/1997 | Granzow | |
| 5,678,290 A | 10/1997 | Good | |
| 5,681,757 A | 10/1997 | Hayes | |
| 5,688,391 A | 11/1997 | Hayes | |
| 5,703,631 A | 12/1997 | Hayes et al. | |
| 5,707,684 A | 1/1998 | Hayes et al. | |
| 5,721,123 A | 2/1998 | Hayes et al. | |
| 5,736,074 A | 4/1998 | Hayes et al. | |
| 5,736,314 A | 4/1998 | Hayes et al. | |
| 5,742,314 A | 4/1998 | Hayes | |
| 5,751,318 A | 5/1998 | Granzow | |
| 5,757,396 A | 5/1998 | Bruner | |
| 5,767,878 A | 6/1998 | Murphy | |
| 5,772,106 A | 6/1998 | Ayers et al. | |
| 5,787,558 A | 8/1998 | Murphy | |
| 5,849,208 A | 12/1998 | Hayes et al. | |
| 5,858,190 A | 1/1999 | Hayes | |
| 5,861,323 A | 1/1999 | Hayes | |
| 5,955,022 A | 9/1999 | Walker et al. | |
| 6,015,083 A | 1/2000 | Hayes et al. | |
| 6,029,896 A | 2/2000 | Self et al. | |
| 6,077,380 A | 6/2000 | Hayes et al. | |
| 6,079,810 A | 6/2000 | Davis | |
| 6,096,558 A * | 8/2000 | Stock | 436/132 |
| 6,114,187 A | 9/2000 | Hayes | |
| 6,170,930 B1 | 1/2001 | Wallace | |
| 6,188,416 B1 | 2/2001 | Hayes | |
| 6,267,724 B1 | 7/2001 | Taylor | |
| 6,319,530 B1 | 11/2001 | Stewart | |
| 6,325,475 B1 | 12/2001 | Hayes et al. | |
| 6,334,851 B1 | 1/2002 | Hayes et al. | |
| 6,334,980 B1 | 1/2002 | Hayes et al. | |
| 6,338,715 B1 | 1/2002 | Hayes et al. | |
| 6,339,897 B1 | 1/2002 | Hayes et al. | |
| 6,367,925 B1 | 4/2002 | Chen et al. | |
| 6,378,988 B1 | 4/2002 | Taylor et al. | |
| 6,390,453 B1 | 5/2002 | Frederickson et al. | |
| 6,435,004 B1 * | 8/2002 | Miller | 73/23.3 |
| 6,440,212 B1 | 8/2002 | Hayes | |
| 6,474,786 B2 | 11/2002 | Percin et al. | |
| 6,620,283 B1 | 9/2003 | Hayes et al. | |
| 6,625,351 B2 | 9/2003 | Cox et al. | |
| 6,642,068 B1 | 11/2003 | Hayes et al. | |
| 6,672,129 B1 | 1/2004 | Frederickson et al. | |
| 6,805,902 B1 | 10/2004 | Hayes | |
| 6,998,074 B1 | 2/2006 | Radulescu | |
| 7,152,984 B1 | 12/2006 | Hayes | |
| 2003/0065294 A1 | 4/2003 | Pickup et al. | |
| 2004/0023413 A1 | 2/2004 | Opalsky | |
| 2005/0268911 A1 | 12/2005 | Cross et al. | |
| 2005/0273016 A1 | 12/2005 | Colman et al. | |
| 2006/0031099 A1 | 2/2006 | Vitello et al. | |
| 2006/0073483 A1 | 4/2006 | White et al. | |
| 2007/0062255 A1 * | 3/2007 | Talton | 73/23.3 |
| 2007/0167853 A1 | 7/2007 | Melker et al. | |
| 2007/0203448 A1 | 8/2007 | Melker et al. | |
| 2007/0261468 A1 | 11/2007 | Crespo et al. | |

OTHER PUBLICATIONS

Hayes, D. J. and Taylor, D. W., "Real Time Calibration and Testing of Chemical Sensors enabled by Precision Micro-dispensing Technology," http://www.microfab.com/about/papers/SPIE_defense_2005.pdf, 2005, 8 pages.

Scholl, P. F., et al., "The Development of Matrix-Assisted Laser Desorption/Ionization Time-of-Flight Mass Spectrometry for the Detection of Biological Warfare Agent Aerosols," John Hopkins APL Technical Digest, 1999, pp. 343-351, vol. 20, No. 3.

Smith, P. J., "An Introduction to Inkjet," Dutch Polymer Institute, http://www.schubert-group.de/PDF/IJWorkshop/IJ_Smith_1.pdf, undated, 25 pages.

"MicroFab Technote 99-01 Background on Ink-Jet Technology," MicroFab Technologies, Inc., Sep. 28, 1999, 4 pages.

Slemeyer, A., "A Depletion Compensated Wet Bath Simulator for Calibrating Evidential Breath Alcohol Analyzers," http://www.icadts.org/proceedings/2000/icadts2000-229.pdf, 2005, 6 pages.

International Search Report, International Patent Application No. PCT/US2009/035898, mailed on Oct. 5, 2009, 11 pages.

* cited by examiner

CALIBRATION AND ACCURACY CHECK SYSTEM FOR A BREATH TESTER

CROSS REFERENCE TO RELATED APPLICATION(S)

This application claims the benefit of U.S. Provisional Patent Application Ser. No. 61/033,218, filed Mar. 3, 2008 and the benefit of U.S. Provisional Patent Application Ser. No. 61/050,823 filed May 6, 2008. The entire disclosure of both documents is herein incorporated by reference.

BACKGROUND

1. Field of the Invention

The present invention relates to systems and methods for providing calibration and accuracy checking for a breath tester. Specifically, utilizing small dispersed drops of alcohol or a water and alcohol mix to simulate exhausted human breath to a breath tester.

2. Description of the Related Art

For the purposes of public safety on the roads and elsewhere, there is a need to make sure that individuals are not operating potentially dangerous machines (such as automobiles) while they are impaired by the effects of alcohol consumption. To try and prevent people from driving drunk, most states have enacted laws which impose fines or other criminal penalties if individuals have a breath or blood alcohol level above a certain amount. In order to effectively enforce these laws, it is necessary to be able to measure the alcohol concentration in human breath and compare the results against legal limits. There are a variety of measuring instruments used for determining the concentration of alcohol in human breath ranging from small hand held devices to larger bench top units and machines built into cars or certain machinery. Since a determination of breath alcohol above the legal threshold can result in criminal penalties, loss of a job, or other sanctions, the accuracy of these instruments is paramount.

Great care and effort is taken by owners and managers of evidential breath testing equipment to ensure proper calibration as well as follow-up accuracy checks at generally regular intervals. In attempts to eliminate the labor time of this testing and concerns about human error in the testing, manufacturers of breath testing equipment often offer automated or semi-automated methods for doing calibrations and accuracy checks. Some users of breath alcohol test equipment, such as Motor Vehicle Law Enforcement, may even require an automatic accuracy check every time they test a human subject and sometimes even before and after the human subject test simply to make sure that the device is reading correctly and will supply court-admissible evidence.

There are generally different standards used when calibrating breath testers. As breath (containing alcohol or not) is a vapor comprising exhalation gases and vaporized substances, instruments that measure alcohol concentration in this breath vapor generally need standards to be provided in a similar form for accurate calibration. Calibration gases of many sorts are well known in many applications including breath testing. In breath testing, the calibration standards are generally of two types, wet and dry. Wet standards include water vapor; dry standards do not. Some argue that wet standards are better because they include moisture like human breath and are therefore more representative. However, commercial providers of both wet and dry standards generally advertise +/−2% accuracy of calculations with actual breath.

In either case, the alcohol concentration of measurement interest is in a carrier gas such as air, breath, or nitrogen. A typical breath ethanol concentration which would result in illegal driving in most states is 200 parts per million (ppm) or more. That is 200 parts ethanol per million parts of carrier gas regardless of the carrier gas composition. Therefore, the standards generally provide samples which contain very close to 200 ppm to make sure the dividing line is correctly calibrated.

Wet standards have a long history in breath testing, are well accepted, and the liquids used in them can be certified by chemical analysis against NIST traceable standards. The standards are prepared by combining known amounts of ethanol and water in a partially filled jar that is accurately heated to 34° C. These heated jars are sold commercially and are referred to as Simulators. At equilibrium, the quiescent headspace above the jar contains a vapor with a known concentration of ethanol along with nearly 100% relative humidity at that temperature.

By introducing sober human breath or air from another suitable source into the jar (by blowing or injecting gas into the liquid) the known concentration of ethanol vapor exits the headspace and can be introduced into a breath tester at which point a measurement may be taken.

Dry standards, by contrast, have no water vapor included with them. This is because dry standards are prepared with carrier gases such as nitrogen or argon and are supplied in pressurized tanks ranging from 500-2500 psi. At these pressures, if water vapor were included in amounts similar to human breath concentrations in practical field use, the water would condense out of the gas, trap ethanol, and cause wholly inaccurate results. The dry gas standards are typically certified by measurement against NIST-prepared standards.

In automated wet testing, the above-mentioned Simulators generally have input and output ports. Typically, a Simulator will sit alongside a breath test machine, normally on a desktop. The output of the Simulator is plumbed into the instrument such that when gas is pumped into the Simulator input (either from a tester blowing into it, or from an associated gas tank or pump), a vapor of known ethanol concentration will be presented for measurement or calibration in the same manner human breath would be. Typically, an electric pump is used to pump ambient air into the Simulator for this purpose. The pump may be internal to the breath tester, part of the Simulator itself, or an entirely separate component. Typically, gas is pumped through a Simulator for 4-10 seconds in order for a measurement to be completed. This pump time varies depending on the flow rate and the amount of instrument volume that has to be purged of ambient gas before a measurement is taken to ensure the measurement is taken of the carrier gas with the correct concentration of ethanol.

Every time a sample is taken from a Simulator, some of the ethanol in the liquid replenishes lost ethanol from the headspace. However, over time, the equilibrium concentration of ethanol provided by the Simulator decreases from its originally intended value as ethanol is slowly lost to the ambient air due to the carrier gas (and the carried ethanol) being exhausted from the breath tester. Some breath test instruments use recirculation systems that take the ethanol vapor provided by the Simulator output, after it exits the breath tester's measurement chamber, or manifold, and pumps it back into the Simulator inlet, instead of using ambient air to provide the simulated exhalation. This greatly reduces any effects of lost ethanol from the Simulator causing lower concentrations to be provided over time since used ethanol is not exhausted to the ambient, but is returned to the Simulator.

Whether using recirculation systems or not, care must be taken to avoid any condensation of water from the Simulator output until the concentration of ethanol is measured by the breath tester. Otherwise, the alcohol in the gas will be less than intended due to ethanol being condensed from the gas. To avoid condensation, various elements or tubes in the instrument are generally heated prior to measurement.

It must be noted that the using Simulators for portable instruments or in on-site calibration tests can be problematic. They are subject to splashing, tipping over, and operate properly within a very limited ambient temperature range due to their complicated design which is necessary for accuracy. Further, they are not really designed for easy or efficient transport, and that tends to limit their use to controlled settings.

The dry gas standards are provided in a variety of types of high-pressure cylinders. A typical size of a tank is approximately 1 liter or more. These cylinders are typically equipped with pressure regulators where the high tank pressure is regulated down to a much lower delivery pressure to the breath tester to better simulate the pressure provided by human breath. Often, an electronic shut-off valve will allow delivery of the low-pressure calibration gas to the measurement chamber on demand.

Compared to wet standards, the dry standards offer some advantages. Dry gas delivery systems generally represent a less complex system hardware design to provide automated calibrations and accuracy checks than the wet standards. The dry gas system is generally easier for instrument owners to manage and maintain and the dry gas system is certainly more amenable to a portable system. Specifically, since the only major components of a dry gas system are the tank and regulator, they are pretty easily portable and are not as affected by movement or situation as wet systems. The dry gas tanks will eventually run empty, but no recirculation system is required to keep the value stable throughout the tank's lifetime.

However, dry gas standards have several factors that complicate their use. First of all, they require a compensation for barometric pressure in the breath tester. The concentration of dry gas standards follow the ideal gas law, and the measured value will change with barometric pressure changes due to elevation or weather. Also, if a dry gas system has a leak, it is possible to lose a significant amount of gas before a problem is noticed. Furthermore, some users (especially mobile ones) have concerns about the safety of transporting even relatively small high-pressure gas tanks which, even while filled with generally nonflammable gas, are potentially explosive due to their high pressure. Lastly, as stated earlier, the dry gas contains no water vapor. Some who are skilled in the art believe that a water component to the calibration gas is essential, because water vapor is a large constituent of human breath and it would therefore be possible to challenge the reading of a breath tester which has only been calibrated using a dry gas system.

SUMMARY

Because of these and other problems in the art, described herein is a calibration and accuracy check system for use with a breath tester. These systems and methods can overcome some or all of the problems inherent in both the wet and dry gas standard systems currently used in the breath tester industry by utilizing a liquid water and alcohol mix similar to that used in a wet simulator, which would be NIST traceable, but which is provided in a generally sealed storage bottle. This mixture is then dispensed as a series of specifically sized small droplets which can be counted to determined the exact composition injected. In an embodiment, this dispensing utilizes a dispensing nozzle and the amplification of induced capillary waves on the fluid to provide for dispersing of a specific number of regularly sized droplets. Essentially, this is the same general dispensing method as is used for dispensing ink in an inkjet print head. Using such a dispensing system, minute drops of this liquid are directly dispensed into an instrument measurement chamber on demand for calibration and accuracy check requirements without need of a carrier gas, or are accurately dispensed into a carrier gas for testing using the standard breath collecting apparatus of the breath tester.

There is described herein, among other things, a calibration system for a breath tester comprising: a storage reservoir containing a mixture of water and an alcohol at known concentration; a dispensing head for dispensing said mixture, said dispensing head including: a nozzle for ejecting said mixture from said storage reservoir; and means for amplifying induced capillary waves into said mixture; wherein said dispensing head can inject said mixture into a reaction chamber of said breath tester.

In an embodiment of the system said means for amplifying comprises a heating element or a piezoelectric element.

In an embodiment of the system, said alcohol comprises ethanol or methanol.

In an embodiment of the system said dispensing head may be connected directly to said reaction chamber or may dispense said mixture into a carrier gas.

There is also described herein, a calibration system for a breath tester comprising: a storage reservoir containing alcohol; a dispensing head for dispensing droplets of known size from said storage reservoir; and a monitoring system for determining the number of droplets dispensed from said dispensing head; wherein said dispensing head dispenses a fixed number of droplets to said breath tester and said breath tester is calibrated based on the resulting concentration of alcohol is based on said fixed number of drops dispensed.

In an embodiment of the calibration system said fixed number of droplets may be dispensed directly to a reaction chamber in said breath tester or may be dispensed into a carrier gas which is then supplied to said breath tester.

In an embodiment of the calibration system the fixed number of droplets may change between successive tests or may change according to a pattern over time.

In an embodiment of the calibration system said storage reservoir also includes water.

In another embodiment of the calibration system the alcohol comprises ethanol or methanol.

There is also described herein, a method of calibration of a breath tester, the method comprising: providing a storage reservoir containing alcohol internal to a breath tester; dispensing a preselected number of droplets of known size from said storage reservoir to said breath tester, determining the breath alcohol level said preselected number of droplets represents; and calibrating said breath tester based on the resulting concentration of alcohol.

In an embodiment of the method, the droplets may be dispensed directly to a reaction chamber in said breath tester.

In an embodiment of the method, the storage reservoir also includes water.

In another embodiment of the method, the alcohol may comprise ethanol or methanol.

DESCRIPTION OF PREFERRED EMBODIMENT(S)

Due to the problems inherent in both the wet and dry gas standard systems currently used in the breath tester industry, there is described herein a calibration and accuracy check system that utilizes liquid alcohol, or a liquid water and alcohol mix similar to that used in a wet simulator, which would be NIST traceable but is provided in a sealed reservoir. This mixture is then dispensed in a series of evenly sized droplets. Using such a dispensing system, minute drops of this liquid may be dispensed directly into the reaction chamber of the breath tester for calibration and accuracy check requirements. This testing can be performed on-demand and under virtually any conditions. The required amount of alcohol is introduced to the measurement chamber without needing to use a carrier gas, although one may be used in an alternative embodiment. Even though the alcohol could be pure, it will generally be diluted with liquid such as water or other liquid components of human breath to provide for generally better repeatability of results and to better simulate human breath.

Figure 1A:
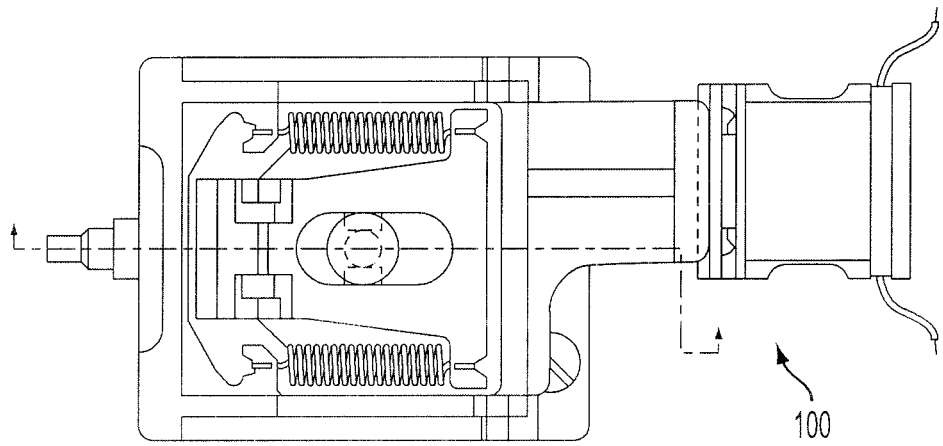
FIG. 1 provides for a prior art fuel cell sampling system in top view (FIG. 1A) and sectioned side view (FIG. 1B).
Figure 1B:
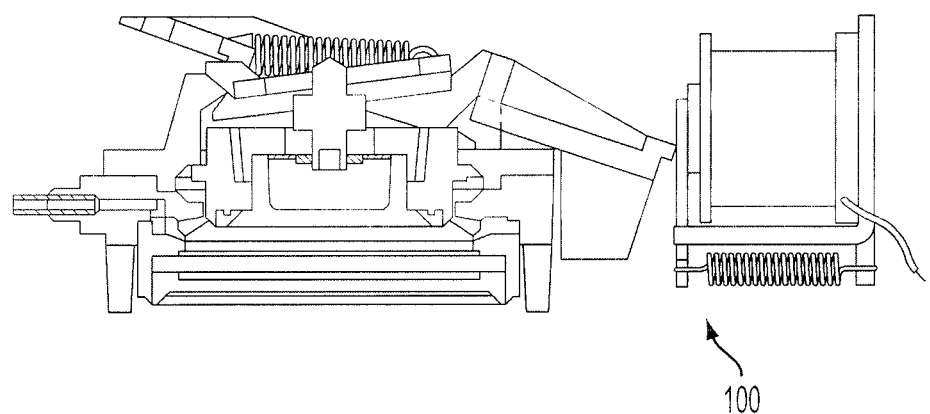
Figure 2A:
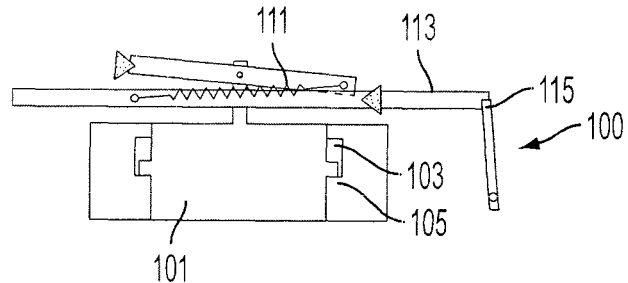
FIG. 2 provides a simplified sectioned side view of the sampling piston portion of the fuel cell sampling system of FIG. 1 in three different positions. A ready or down position (FIG. 2A), the energized sampling position (FIG. 2B), and an up position where the sample is in the reaction chamber (FIG. 2C).
Figure 2B:
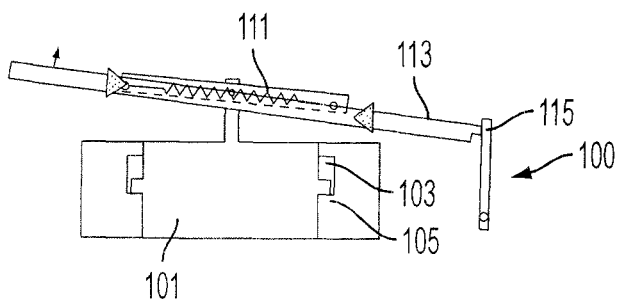
Figure 2C:
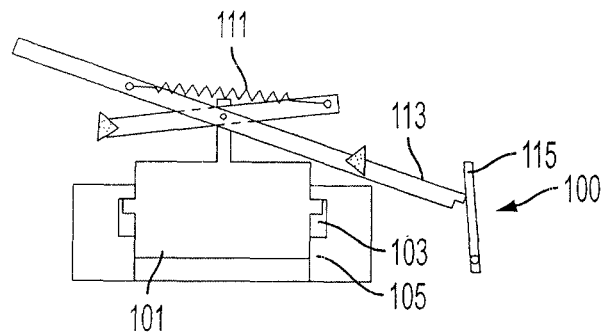
Figure 3:
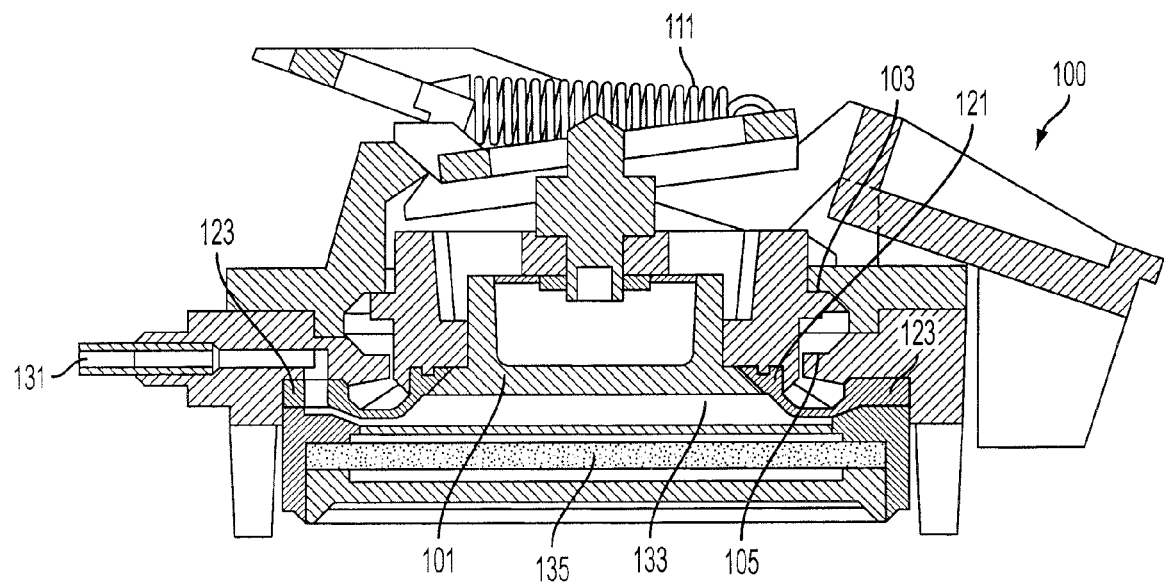
FIG. 3 provides the sectioned side view of FIG. 1 enlarged with component labeling.

In an embodiment, when a sample (such as breath or calibration gas) is introduced into a fuel cell or other measurement chamber, the sample typically undergoes a chemical reaction such as, but not limited to, a catalytic reaction and electrons are given off in proportion to the alcohol concentration so long as the sample size is fixed. FIG. 1 provides an example of a prior art fuel cell sampling system (100) and would be common in an alcohol breath tester of current known design. This particular sampling system (100) is not meant to define the only type of sampling system with which the calibration and accuracy testing systems and methods discussed herein may be used, but is meant to simply illustrate one exemplary embodiment. In the embodiment of FIG. 1, there is a top view provided as FIG. 1A and a sectioned side-view as FIG. 1B. A simplified and sectioned schematic view of the mechanism is shown in FIG. 2 in three different positions (FIG. 2A, FIG. 2B and FIG. 2C) which show the sampling operation of obtaining a sample from an associated manifold and placing it in the reaction chamber (133) for testing. In FIG. 3, the sectioned side view of FIG. 1 at the position of FIG. 2C is enlarged and shown with additional components. These FIGS. will all be discussed together.

The primary movement of the sampling system (100) is a centrally located piston (101) which moves up against an upper stop (103) and down against a lower stop (105). When the piston (101) is in the down position as shown in FIG. 2A, the sampling mechanism is cocked. The bi-stable spring mechanism (111) at the top of the piston (101) is at rest with one of the arms (113) resting on the edge of a spring-loaded armature (115) next to an electromagnetic coil. This is the pre-testing state. When the coil is energized, the armature (115) moves towards the coil (to the right in the FIG.) and the lever arm (113) is released as shown in FIG. 2B, which provides for a sample to be pulled from the inlet (131) into the sample chamber. The springs (111), in turn, pull the piston (101) up against the upper stop (103) as shown in FIG. 2C, which has now had an entire sample placed in the reaction chamber (133) and is ready to commence testing of the sample.

FIG. 3 shows that the piston (101) is in turn connected to the top of a diaphragm (121), anchored at its periphery (123). When the piston (101) goes up, the center of the diaphragm (121) is pulled up creating a vacuum and a gas sample is sucked in through the sample inlet (131) (generally from a breach manifold or other collection system) into a gas reaction chamber (133) between the diaphragm and the face of a fuel cell (135). The time for the sampling to occur is generally a fraction of a second. In a standard fuel cell testing embodiment, the entire assembly is roughly 1½" square and the total volume of the sample taken is a known pre-set amount of approximately 1 cubic centimeter.

The sampling piston (101) is generally operated between the two fixed mechanical stops (103) and (105) to maximize the repeat accuracy of the pump stroke in pulling in a sample of fixed size. In the down position as shown in FIG. 2A, the piston (101) face (and thus the diaphragm (121)) will generally nearly touch the fuel cell (135) face so as to minimize the amount of ambient air in the gas reaction chamber (133). The piston (101) will generally only travel approximately 0.07 inches between the down and the up position. Prior experiments have generally indicated that the sample volume taken in is repeatable and consistent with a less than 0.3% change between sample sizes providing a high level of accuracy in determining the alcohol present in the larger "breath" from which the sample is taken.

Figure 6:
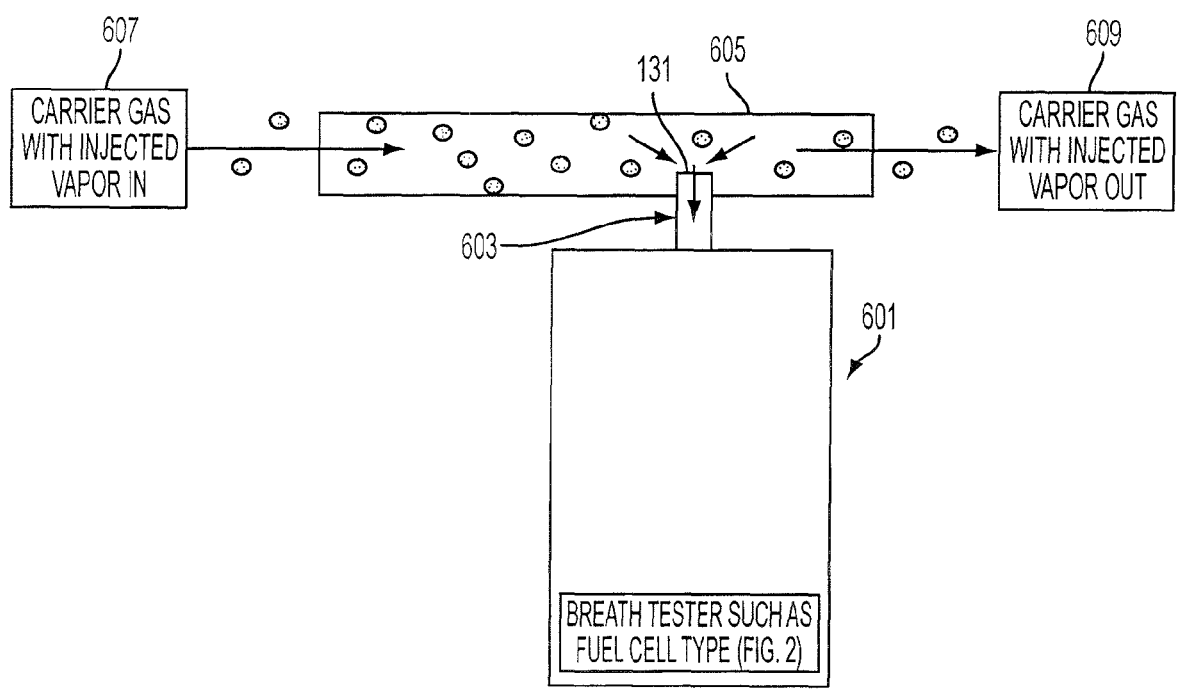
FIG. 6 provides an embodiment of a discrete breath tester used in combination with the calibration system of FIG. 5.

In the embodiment of FIGS. 1-3, the sampling inlet (131) generally protrudes into a manifold (605) of flowing gas from which it withdraws the sample for analysis, as is generally shown in FIG. 6. The flowing gas may be human breath in the case of an alcohol breath test or it might be either a wet or dry gas standard for instrument calibration or accuracy check. Generally, the manifold (605) will comprise a sealed pathway which is designed concentrate the breath into a flowing stream for testing purposes. In order to make sure that a good sample is collected from a human using the breath tester, the stream therefore includes significantly more gas than will be pulled into the reaction chamber (133). Thus, the amount of gas which is fed into the manifold (605) is vastly greater than the amount of gas put into the reaction chamber (133). This gas is exhausted out the end of the manifold (605) to the ambient air at a level hundreds of times greater than the small amount which is actually brought into the reaction chamber (133) for analysis.

Figure 4:
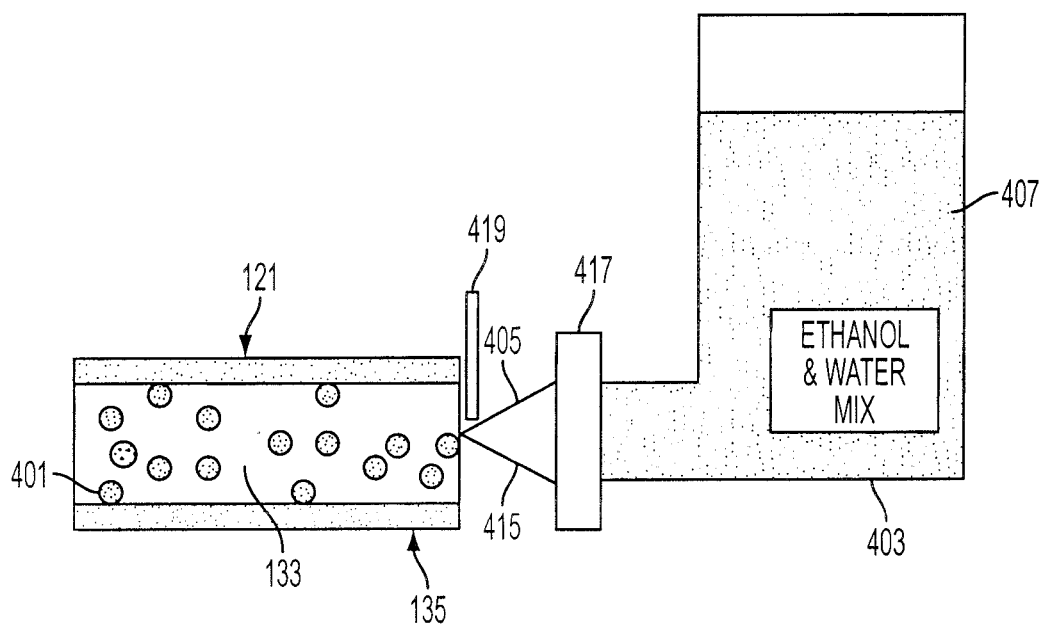
FIG. 4 shows how to utilize a dispersed fluid jet to provide vapor simulative of breath directly to a fuel cell reaction chamber.

With reference to the fuel cell sampler shown in FIGS. 1-3 and particularly FIG. 3, FIG. 4 shows a first embodiment illustrating how a test sample of material may be provided on demand. Specifically, in the embodiment of FIG. 4 the piston (101) and thus the diaphragm (121) are placed in the UP position of FIG. 2C. This may be obtained by placing the device in a calibration mode where the reaction chamber is adjusted but no sample, or simply a sample of ambient air, is pulled into the reaction chamber (133) from the inlet. Droplets (401) of alcohol and/or any other liquid (407) are fed directly and on demand to the reaction chamber (133) from a holding vessel (403) through a dispensing head (405).

The dispensing head (405) is designed to provide for a number of evenly sized droplets of liquid. Specifically, the drops (401) will be of a specific predetermined size and the action of supplying them will result in a specific number of drops (401) being provided. In another embodiment, the number of drops (401) is counted by a monitoring system (419) to determine the number dispensed in this test. Thus, any variation in the specific number between tests can be determined. The monitoring system (419) may comprise any system or means known to one of ordinary skill in the art for determining the number of droplets (401) dispensed including but not limited to microprocessor controls, hard wired circuits, or hardware counting mechanisms. Consequently, the automatic instrument calibrations and accuracy checks performed by the breath tester (100) will be highly accurate and require a much smaller amount of calibration material to be used per test. Firstly, there is no gas wasted in such an embodiment as all liquid material (407) is injected directly into the reaction chamber (133) which had already taken in the necessary "carrier" gas by being moved into the position of FIG. 2C. Secondly, the amount of alcohol injected with each test can be determined to a high degree of accuracy.

In an alternative embodiment, the liquid may be injected into the reaction chamber (133) while the piston (101) is in the position of FIG. 2A where the reaction chamber is much smaller but remains still and is filled with a "carrier" gas (generally air) which is in an ambient state. In either embodiment, gas (and carried liquid) is not exhausted to ambient during calibration. Since the injected material is alcohol or alcohol and water, the standard source can be continually supplied at low cost. The vessel (403) may be provided in a sealed or refillable form internal to the encasement of the device and thus is available at any time and at any location. Thus the device may be calibrated and/or tested for accuracy at any time. Further, since the liquid (407) is directly injected into the reaction chamber (133), there is virtually no possibility of condensation in the air path, and therefore the concentration is clear, repeatable and determinable.

To provide for the concentration to be fixed, it is desirable to be able to control two features of the dispensing head's (405) dispensation. Specifically drops (401) are to be of a known size (so each includes a known amount of liquid) and the number of drops (401) dispensed needs to be determinable for each test. In an embodiment, those facets of the droplets (401) are determined by using a nozzle (415) for dispensing in conjunction with a means (417) for inducing capillary waves on the liquid (407). In order to induce the capillary waves on the fluid droplets (401), a wide variety of methods and means may be used. These include, but not limited to, piezo-type or resistive heating devices which can be used for such purpose as is know to those of ordinary skill in the art. Specifically, these devices will generally cause the liquid (407) to be ejected from the nozzle (415) in a jet of known (and consistent) sized droplets (401). Depending on the specific design of the inducement device (417) and nozzle (405), the drop (401) sizes of the liquid (407) may vary, as might the rate of production of the drops. So as to insure that the specifically desired amount is dispensed, the breath tester (100) may also include an electronic control or monitoring system (419) which will seek to provide a certain number of certain sized drops (401) to be dispensed on demand.

The combination of the number of drops (which is the total volume of calibration gas and/or aerosol supplied) (401) and the concentration of the alcohol in the liquid (407) will determine what amount of alcohol presented to the fuel cell (135) for reaction. This can be made equivalent to the same amount of alcohol that might be introduced by taking a 1 cc sample of a wet or dry gas standard of the prior art or may comprise a different amount for different calibration or accuracy checking purposes.

In an embodiment, the monitoring system (419) may have the capability to vary the number of drops (401) on demand (such as by determining how many individual drops aye formed). In this embodiment various equivalent standards might be presented to the fuel cell (135), performing, for example, an automatic linearity test to make sure that the breath tester (100) is accurately determining a range of values. Because some users of breath testers will find it beneficial to perform accuracy and calibration tests at more than one gas concentration, this not only allows for the breath tester calibration to be performed wherever and whenever is needed, but can allow for a variety of tests to be performed at the same time.

The vessel (403) may contain pure alcohol but in the depicted embodiment it does not contain pure alcohol, but includes a known concentration of alcohol mixed with water and/or other liquids commonly found in human breath. Pure alcohol is extremely hygroscopic and therefore difficult to handle without it immediately taking on water. A mixture with water is more stable and therefore can provide for easier and longer term storage of the breath tester. Also, the more dilute the alcohol/water mixture is, the more drops (401) will be required per calibration sample resulting in larger samples needing to be produced for the same concentration. Up until a limit, a larger sample will generally make the system more accurate as a delivery error of one drop will have far less effect on the total alcohol delivered if the alcohol has been heavily diluted with water.

The dispensing head (405) would generally inject the alcohol, water, or other liquid at a calculated rate that would provide a specific concentration of one or more substances such as, but not limited to, ethanol; ethanol & water; methanol; or methanol & ethanol & water. These are just a few examples of liquids (407) or combination of liquids (407) that could be injected into the reaction chamber (133) and can be stored in the vessel (403). There could be one or many heads (405), each with their own vessel (403) of liquid (407). The liquid (407) in multiple vessels (403) could be duplicative, so as to provide for possible independent verifications of any reading from any one vessel (403), or could include different materials so as to provide for different tests.

In an embodiment, the different liquids (407) could be used to provide for different types of testing. For example, the testing could be to detect specific interfering substances. That is, the different heads (405) could provide the same sample sizes, but using different mixtures (407). Alternatively, the different heads (405) could produce different sample sizes with different mixtures (407). In an embodiment, this would provide for a further accuracy check as the same net alcohol amount could be provided in two different samples. One sample could be a smaller amount of a higher concentration, and the other a larger amount of a lower concentration. If the breath tester (100) read both samples identically and accurately, its calibration could be further confirmed.

Depending on the exact head (405) technology and instrument design, the reservoir (403) may need to be heated to keep the mixture (407) at a known density. It might also need to be vented in some fashion. In an embodiment, this venting could comprise a one-way check valve to always equalize pressure in the vessel (403) with ambient pressure. Alternatively, a pressure may be applied to the reservoir (403) as it empties so as to maintain the mixture (407) at a constant determinable state. In order to maintain such a pressure, or simply to determine how full the reservoir (403) is, sensors may be associated with the reservoir (403). In an embodiment, such sensors can also be used to determine orientation of the vessel (403), and therefore make sure that a correct fluid amount is fed to the head (405) in each test as well as to determine the fill level and equalize the pressure and/or notify a user that the vessel (403) needs refilling.

Depending on a variety of design factors, the drops (401) may be delivered to the reaction chamber (133) as tiny drops of liquid that attach to the fuel cell (135) in liquid form or they may almost instantaneously transform to vapor as they exit the head (405) and be essentially delivered to the reaction chamber (133) as a vapor in conjunction with air or other gas being present.

The generally preferred design will include little or no dead space between the nozzle (415) exit and the reaction chamber (133) so as to prevent drops (401) from contacting or adhering to any form of carrier component. In this way, drops (401) are not lost in transit but all drops (401) created by the head (405) make it to the reaction chamber (133). There are a variety of ways the head (405) can be oriented compared to the fuel cell (135) surface and while the embodiment of FIG. 4 shows it being arranged at the side, this is by no means required. There may be advantages to one orientation or another specifically to provide for reservoir (403) being positioned within the housing of the breath tester (100) which will generally depend on the type of breath tester (100) being used and the relative positioning of the components.

The principles and embodiments discussed herein could be used for a variety of sensors besides fuel cells as the sample providing mechanism and method is independent of the type of sensor it is used with. Sensors that require much larger volumes of calibration gas (flowing or quiescent) may require that the head (405) further include a gas feeder whether as a part of the fluid feed or as a separate feed. Further, the designs, embodiments, and principles discussed here can be used in applications beyond breath alcohol testing, including without limitation, providing calibration for other mechanical "sniffer" devices which are designed to sample gases and detect small concentrations of liquid materials therein.

It is well known that the biggest cause of fuel cell (135) aging, where aging means both calibration drift and increasingly longer time to give a result, is the loss of water content in the fuel cell (135) material. Specifically, the cell (135) will dry out over time and have much more trouble reading. The systems and methods described herein could also be easily used to automatically inject liquid into the reaction chamber (133), and thus to the fuel cell (135) from time to time to keep the fuel cell (135) hydrated. In such an embodiment, it is preferred that there be a second vessel (403) having only water therein so as to prevent an inaccurate reading from alcohol being left sitting in the reaction chamber (133). The pure water head (405) could then be used to re-hydrate the fuel cell (133) either on-demand or according to an automated schedule.

Dispensing systems such as those contemplated above could also be used for applying other reference chemicals to the sensor (135) to facilitate the detection of "interfering substances" or calibrating the detection of such substances. Those skilled in the art understand that sensors might have cross-sensitivity to compounds that might be expected in the breath, the presence of which could result in the breath tester (100) producing an inaccurate result. The ability to calibrate the breath tester (100) to deal with the presence of such substances can further increase its accuracy.

The vessel (407) and dispensing head (405) contemplated herein would generally be significantly smaller than a dry gas tank or a wet simulator, thus making it advantageous for use in portable as well as fixed-location equipment. Furthermore, the power required to operate this apparatus would be much less than that required to operate a wet bath Simulator (which typically requires heaters and stirrer motors) as well as being significantly easier to use and more stable. As mentioned above, these systems do not require high pressure gas to be stored, thus removing a safety concern with dry gas standards. Further, it is highly likely that such a system could be enclosed in the same housing as the remaining components of the breath alcohol tester (100) and thus would be highly convenient for use at any time.

Those skilled in the art understand that some breath tester governing authorities require use of "external" standards for calibration and accuracy checks. Some authorities might not consider this system as an "external" standard completely independent of the instrument since the head (405) and vessel (403) are designed to interact directly with the reaction chamber (133). While the dispensing system is exterior to the operational parts of the instrument (that is external to the reaction chamber (133)), the vessel (403) and head (405) may be arranged internal to the housing of the breath tester (100) and thus be "internal" to the instrument. While external standards may be required in some instances, there is also a history of using "internal" standards in some instances, situations, and jurisdictions. These are routinely used in the field as accuracy checks, even though external standards may be required for formal calibrations to provide for improved certainty of results.

Figure 5:
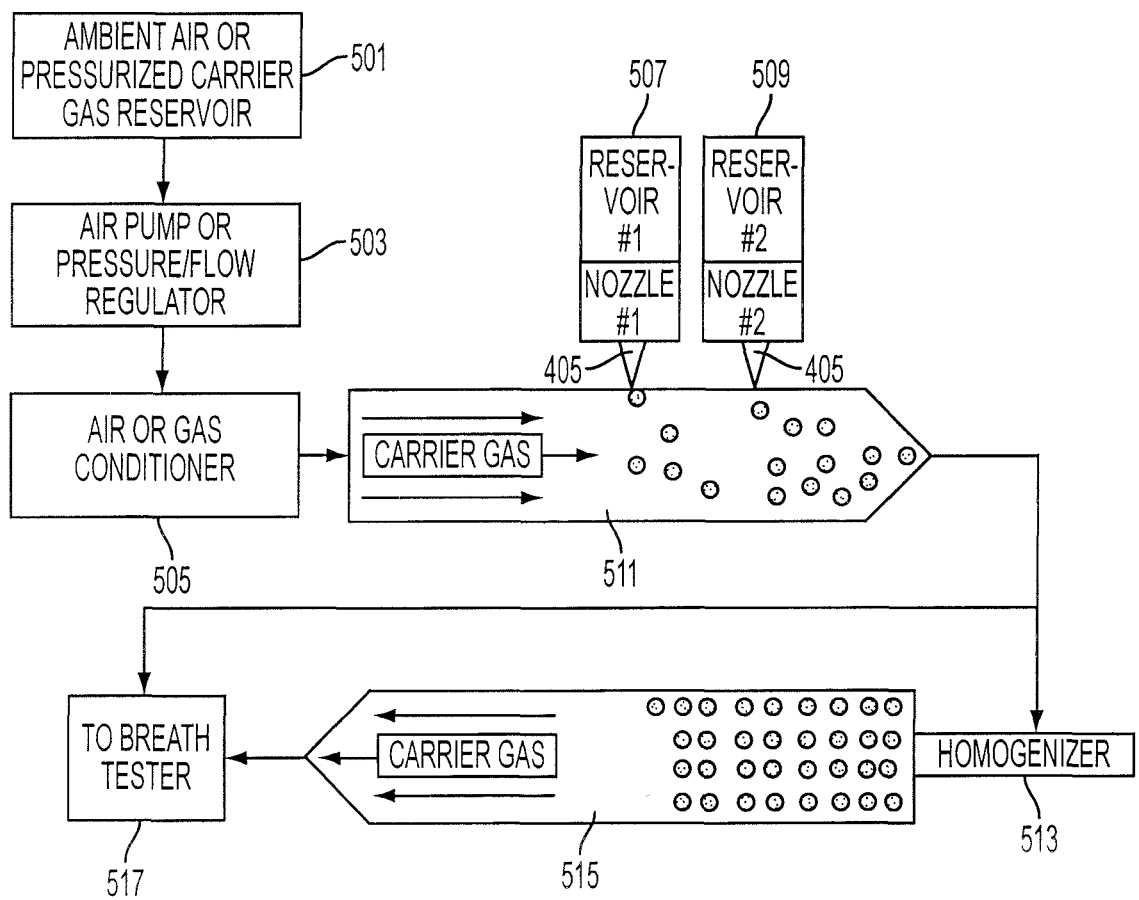
FIG. 5 provides an embodiment of a calibration system using a dispersed fluid jet with a carrier gas.

While the above embodiment contemplates use of the liquid jet without a carrier gas being used, the principles, systems, and methods discussed above may also be used in an embodiment with a carrier gas, such as in the embodiment of FIG. 5. This embodiment could be used as an internal standard but would more likely be used as an external standard such as may be required to meet such regulations on testing. This embodiment is not meant to be separate from the principles, systems, and methods discussed above, but builds on, the above description as well as using some or all of its aspects as described above.

In an embodiment a carrier gas (511) is utilized (so as to be an external standard). The carrier gas (511) is generally air, but the embodiment does not mean to rule out other carrier gases and nitrogen or other carrier gases could be used in alternative embodiments. The air could be conditioned air that is heated, dehumidified, or exposed to some other conditioning by an air conditioning system (505) prior to having the ethanol and/or water injected therein to make sure it has expected properties.

In one embodiment, the air would be supplied, presumably by a pump (503), at a constant flow rate from the ambient (501) to eliminate the need for a compressed tank. However, other methods that provide a constant flow rate or constant mass flow rate could be used. For example, regulated delivery from a pressurized tank of carrier gas (511) could be used. In a still further embodiment, a pump (503) could be used to present an approximately known flow rate and a mass flow sensor or flow sensor could be used to measure the exact mass flow rate or flow rate in order to calculate the exact rate the dispensing system should deliver drops in order to produce a precise and desired concentration. A similar feedback system could be used with pressurized carrier gas as well.

Heads (405) would inject the alcohol (507), water (509), or other liquid at a calculated rate that, in conjunction with the flow of carrier gas (511), would provide a specific concentration of one or more substances such as, but not limited to, ethanol; ethanol & water; methanol, or methanol & ethanol & water into the carrier gas stream (511). As in the depicted embodiment, there could be one or many dispensing heads (405), each with their own reservoir of liquid to provide for independent mixing as the material is provided to the carrier gas (511), or the various dispensing heads (405) may be provided with premixed samples. In the latter embodiment, fewer heads (405) will generally be required, which can simplify the system; however, providing for more specific alternative concentrations can be more difficult. The liquid (507) or (509) in multiple reservoirs could be duplicative or each could be different depending on the desired outcome.

In the embodiment where different fluids are each provided with their own dispensing head (405), the different liquids could be added at different rates at different times to provide a variety of vapor concentrations. Further, the rates of injection could be varied in real time in order to provide a profile over time of changing concentrations of one or more substances in the carrier gas (511).

While the carrier gas (511) and fluid mixture may be provided to the breath tester (517) at this point, it may be required, in some embodiments, that the substance be carried as a vapor in the carrier gas (511) and not as an aerosol which may be produced by the dispensing head (405). Some turbulence may, therefore, need to be added to the flow in order to produce complete homogeneity of the mixture. In the embodiment of FIG. 5 the output carrier gas (511) with the fluid therein is fed into a homogenizer (513) so as to provide a more homogenized carrier gas/fluid mixture (515) (that is, a vapor) which is then provided to the breath tester (517). Other conditioning of the flow may be required such as heating or pressure change in order to produce homogeneity of the mixture (515) which may be performed by the homogenizer (513).

To use the output carrier gas (515) of the embodiment of FIG. 5, the carrier gas (515) (and thus the carried liquid) may be provided to a breath tester by variety of different methodologies. In FIG. 6 there is shown a breath tester (601) which takes a discrete small sample for analysis at an instant in time during a human subject's exhalation. This type of tester (601) typically includes a sampling port (603) with inlet (131) that protrudes into a mouthpiece or manifold (605) of flowing gas. The manifold (605) may be a permanent part of the breath tester (601) or may be a temporary manifold such as a disposable mouthpiece (605) temporarily mounted on a breath tester's sampling port (603). In a still further embodiment, the manifold (605) could be a part of a testing system that temporarily connects to the breath tester (601) such as to replace such a disposable mouth piece (605). In this embodiment, the flowing gas (607) into the manifold (605) of whatever description could be a designed concentration of a known vapor in a carrier gas (515) as would be produced in FIG. 5. As this carrier gas (515) is passed through the manifold, the breath tester (601) will obtain a sample through the inlet port (603) and (131) in the standard fashion. The gas which is not utilized is then exhausted (609) from the manifold (605).

Figure 7:
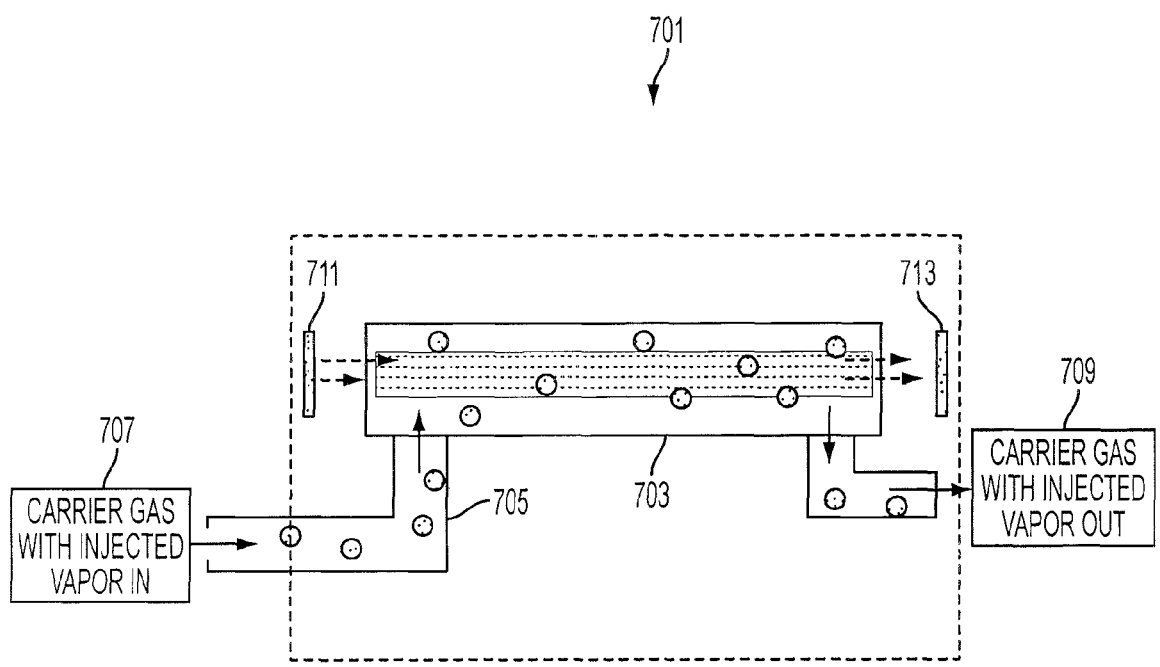
FIG. 7 provides an embodiment of a continuous breath tester in combination with the calibration system of FIG. 5.

A second type of Breath Tester (701) makes a continuous analysis in real time during a human subject's exhalation and an example is shown in FIG. 7. This tester (701) typically includes a measurement chamber (703) through which all the flowing gas (707) passes through. There is connecting tubing (705) which directs the gas (707) into and out of (709) the chamber (703). In the chamber (703) a measurement system such as one utilizing an infrared source (711) and detector (713) can then be used. In this embodiment, the carrier gas (707) can be continuously provided having either a fixed concentration or a varying concentration of known variance to provide for the carrier gas (707) to be tested in the chamber (703).

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A calibration system for a breath tester comprising:
  a storage reservoir containing a mixture of water and an alcohol at known concentration;
  a dispensing head for dispensing said mixture, said dispensing head including:
    a nozzle for ejecting said mixture from said storage reservoir; and
    means for amplifying induced capillary waves into said mixture;
  wherein said dispensing head injects said mixture directly into a reaction chamber of said breath tester.

2. The system of claim 1 wherein said means for amplifying comprises a heating element.

3. The system of claim 1 wherein said means for amplifying comprises a piezoelectric element.

4. The system of claim 1 wherein said alcohol comprises ethanol.

5. The system of claim 1 wherein said alcohol comprises methanol.

6. The system of claim 1 wherein said dispensing head dispenses said mixture into a carrier gas.

7. A combination calibration system and breath tester comprising:
  a breath tester, said breath tester comprising:
    a as reaction chamber;
    a manifold for accepting a human breath;
    a sampling inlet, said sampling inlet connecting between said gas reaction chamber and said manifold; and
    a sampling piston, operation of said sampling piston forcing a sample of material from said manifold, through said sampling inlet, and into said gas reaction chamber;
  a calibration system, said calibration system comprising:
    a storage reservoir containing alcohol;
    a dispensing head for dispensing droplets of known size from said storage reservoir; and
    a monitoring system for determining the number of droplets dispensed from said dispensing head;
  wherein said dispensing head dispenses a determinable number of droplets to said gas reaction chamber without said sampling piston operating and said breath tester is calibrated based on the resulting concentration of alcohol in said number of droplets dispensed.

8. The calibration system of claim 7 wherein said number of droplets are dispensed into a carrier gas which combination is then supplied to said gas reaction chamber.

9. The calibration system of claim 7 wherein said number of droplets changes between successive tests.

10. The calibration system of claim 7 wherein said number of droplets changes according to a pattern over time.

11. The calibration system of claim 7 wherein said storage reservoir also includes water.

12. The calibration system of claim 7 wherein said alcohol comprises ethanol.

13. The calibration system of claim 7 wherein said alcohol comprises methanol.

14. A method of calibration of a breath tester, the method comprising:

providing a storage reservoir containing alcohol internal to a breath tester;

dispensing a determinable number of droplets of known size from said storage reservoir directly to a gas reaction chamber in said breath tester;

determining said number of droplets entering said gas reaction chamber;

determining the breath alcohol level said number of droplets represents; and calibrating said breath tester based on the resulting concentration of alcohol.

15. The method of claim 14 wherein said storage reservoir also includes water.

16. The method of claim 14 wherein said alcohol comprises ethanol.

17. The method of claim 14 wherein said alcohol comprises methanol.

* * * * *